(12) United States Patent
Bódi et al.

(10) Patent No.: US 8,183,402 B2
(45) Date of Patent: May 22, 2012

(54) INDUSTRIAL METHOD FOR THE SYNTHESIS OF 17-ACETOXY-11β[4-(DIMETHYLAMINO)-PHENYL]-21-METHOXY-19-NORPREGNA-4,9-DIEN-3,20-DIONE AND THE KEY INTERMEDIATES OF THE PROCESS

(75) Inventors: József Bódi, Budapest (HU); György Visky, Budapest (HU); János Széles, Budapest (HU); Sándor Mahó, Budapest (HU); Csaba Sánta, Budapest (HU); János Csörgei, Budapest (HU); Zoltán Tuba, Budapest (HU); László Terdy, Budapest (HU); Csaba Molnár, Budapest (HU); Antal Aranyi, Érd (HU); Zoltán Horváth, Rácalmás (HU); Gábor Balogh, Budapest (HU)

(73) Assignee: Richter Gedeon Nyrt., Budapest (HU)

( * ) Notice: Subject to any disclaimer, the term of this patent is extended or adjusted under 35 U.S.C. 154(b) by 407 days.

(21) Appl. No.: 12/598,163

(22) PCT Filed: Jun. 19, 2008

(86) PCT No.: PCT/HU2008/000073
§ 371 (c)(1),
(2), (4) Date: Oct. 29, 2009

(87) PCT Pub. No.: WO2009/001148
PCT Pub. Date: Dec. 31, 2008

(65) Prior Publication Data
US 2010/0137622 A1    Jun. 3, 2010

(30) Foreign Application Priority Data
Jun. 27, 2007    (HU) ................................. 0700439

(51) Int. Cl.
C07J 5/00    (2006.01)
C07J 3/00    (2006.01)
(52) U.S. Cl. ...................... 552/595; 552/610
(58) Field of Classification Search .................. 552/595, 552/610
See application file for complete search history.

(56) References Cited

U.S. PATENT DOCUMENTS
6,900,193 B1    5/2005    Kim et al.

FOREIGN PATENT DOCUMENTS
WO    97/41145        11/1997
WO    01/47945 A1    7/2001
WO    01/74840 A2    10/2001

*Primary Examiner* — Barbara P Badio
(74) *Attorney, Agent, or Firm* — Jason D. Voight

(57) ABSTRACT

The present invention relates to a process for the synthesis of the 17-acetoxy-11β-[4-(dimethylamino)-phenyl]-21-methoxy-19-norpregna-4,9-dien-3,20-dione of formula (I):

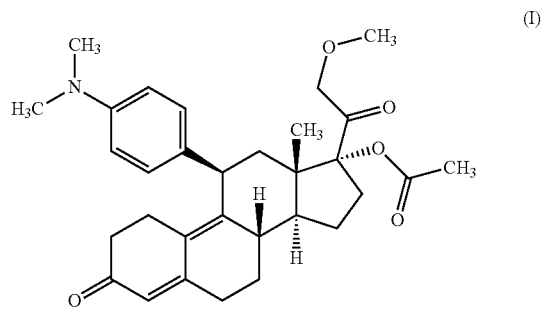

from 3,3-[1,2-etandiyl-bis(oxy)]-oestr-5(10),9(11)-dien-17-one of formula (II):

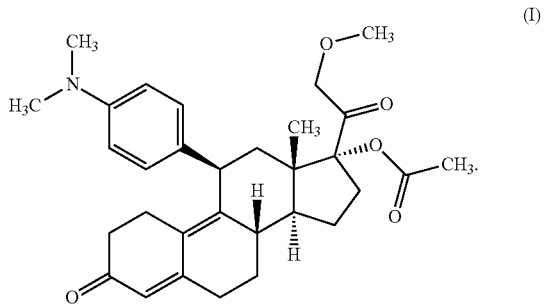

5 Claims, No Drawings

INDUSTRIAL METHOD FOR THE SYNTHESIS OF 17-ACETOXY-11β[4-(DIMETHYLAMINO)-PHENYL]-21-METHOXY-19-NORPREGNA-4,9-DIEN-3,20-DIONE AND THE KEY INTERMEDIATES OF THE PROCESS

This is the National Stage of International Application PCT/HU2008/000073, filed Jun. 19, 2008.

The present invention relates to a process for the synthesis of the known 17-acetoxy-11β-[4-(dimethylamino)-phenyl]-21-methoxy-19-norpregna-4,9-dien-3,20-dione (further on CDB-4124) of formula (I)

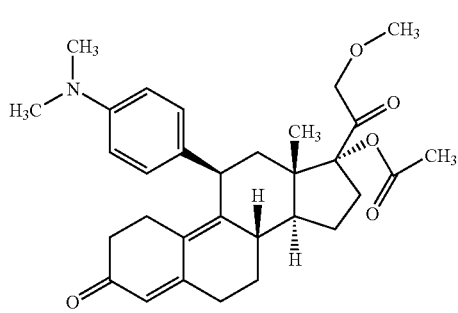

(I)

from 3,3-[1,2-etandiyl-bis(oxy)]-oestr-5(10),9(11)-dien-17-one (further on keto-ketal) of formula (II).

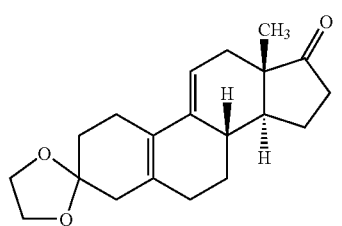

(II)

Compound CDB-4124 belongs to the group of anti-hormones. Anti-hormones can deactivate the effect of hormones in the organism by inhibiting the binding of hormones, for example male and female sex-hormones or hormones produced by the adrenal gland, to the binding place of the target organ, therefore those functions which are induced by hormones can be blocked by administering anti-hormones.

Those compounds which inhibit the synthesis of progesterone or the binding thereof to the receptor can potentially be used in contraception and in those pathological cases, where progesterone plays a role.

An ideal anti-progestogen compound:
specific (it binds only to that receptor, which should be blocked),
it has high affinity to the receptor and its dissociation is slow,
it does not have other biological or pharmacological effect.

The first anti-progestin used in the clinics was described in 1981 [EP 57115], the name of which was mifepriston. Since then several analogues were synthesized and the structure activity relationship of the compounds was examined, particularly the selectivity, mainly the ratio of the anti-progestin and anti-glucocorticoid activity. Currently none of the known anti-progestogen compounds fulfills entirely the selectivity requirements.

Compound CDB-4124, which can be synthesized according to the process of our invention, is such a promising compound according to clinical examinations carried out so far the economical synthesis of which on industrial scale is expedient.

There are several methods in the literature for the laboratory synthesis of CDB-4124 of formula (I), which differ in the starting materials or in the order of the reaction steps. The synthesis of different functional groups is carried out with similar methods. The characteristics of these synthetic methods are that usually they do not take into consideration the safety conditions of the scale up of the process, especially the flammability of the solvents (reaction media), that these solvents can be destructive to health and that some reagents can be expensive.

The aim of the first syntheses was to synthesize that amount from compound/compounds, which was enough to carry out the pharmacological tests. Further development is necessary to provide the purity requirements for the therapeutic use of a compound. The industrial realization of an economical synthesis is usually a modification of the original process or processes or it can be an improved synthesis.

The first synthesis of compound CDB-4124 was described in the patent WO 97/41145, the subject of which was the synthesis of 11β- and 21-substituted 19-norprogesteron derivatives and analogues thereof. These compounds have significant antiprogestogen activity. Scheme 3 illustrates the synthesis of compound CDB-4124.

The starting material of the synthesis was 17α-[(bromo-methyl)-dimethyl-silyl-oxy]-3,3-[1,2-etandiyl-bis-(oxy)]-5(10),9(11)-dien-17β-carbonitrile, which could be obtained from the commercially available 3,3-[1,2-etandiyl-bis-(oxy)]-17α-hydroxy-oestr-5(10),9 (11)-dien-17β-carbonitrile (Davos Chemical Inc. in New Jersey) in 69.5% yield by silylating the hydroxyl group in position 17 with (bromo-methyl)-dimethyl-silyl chloride. The purification was carried out by flash chromatography.

The starting material was reacted with lithium diisopropyl amide in tetrahydrofuran solution at −78° C. and the isolation of the product was carried out by extraction with ethyl acetate and purification with ether. The 21-bromo compound obtained in 60.4% yield was reacted with potassium acetate (99%), then hydrolyzed with potassium hydrogencarbonate to furnish the 21-hydroxy derivative in 57.6% yield.

To protect the keto groups in position 3 and 20 bis-ketal formation was used (in 62.5% yield).

The key step of the synthesis the 21-monomethylation of the 17α, 21-dihydroxy derivative, which was protected in positions 3 and 20, was carried out in the presence of a 1:1 mixture of trimethyl-oxonium-(tetrafluoro-borate) salt and "proton-sponge" [1,8-bis-(dimethylamino)naphthalene]. The obtained product—3,3;20:20-bis[1,2-ethandiyl-bis(oxy)]-17-hydroxy-21-methoxy-19-nor-pregna-5(10),9(11)-diene—was isolated from dichloromethane in 79% yield and used in the next step.

The epoxide formation on the double bond in position 5(10) of the obtained crude 21-methoxy derivative was carried out with hydrogen peroxide in the presence of hexafluoroacetone trihydrate. According to NMR spectroscopy the obtained product contained four types of epoxides. (The main product was 5α,10α-epoxide in 66%.)

The obtained crude mixture of epoxides was used in the Grignard reaction catalyzed by copper(I) ion. After isolation from ether solution the product was purified by flash column chromatography. The hydrolysis of the diketal protective group of the 11β-[4-(dimethylamino)-phenyl] derivative was carried out with a 3:1 mixture of trifluoroacetic acid—water in tetrahydrofuran. The product was obtained in 96.3% yield after extraction with dichloromethane, concentration and treatment of the oily residue with water.

The final step of the synthesis was the acetylation of the hydroxyl group in position 17, which was carried out with a mixture of trifluoroacetic anhydride and acetic acid in dichloromethane in the presence of p-toluenesulfonic acid catalyst at 0° C. After completion of the reaction the mixture was diluted with water, neutralized with ammonium hydroxide solution, extracted with dichloromethane and washed with brine. The combined organic layers were concentrated and the residue was purified by flash column chromatography to obtain compound CDB-4124 in 75.8% yield.

The starting material of the synthesis described in the above patent was 17α-[(bromo-methyl)-dimethyl-silyl-oxy]-3,3-[1,2-etandiyl-bis-(oxy)]-5(10),9(11)-dien-17β-carbonitrile, which was synthesized from keto-ketal by addition of cyanide ion followed by silylation of the hydroxyl group. The 17-silyl-oxy-bromo compound was transformed into 21-bromo derivative with lithium diisopropyl amide at −78° C. Introduction of the methoxy group into position 21 was carried out via indirect way through several steps—21-bromo compound, 21-acetoxy derivative—via the 21-hydroxy compound—using 6 equivalent (relative to the starting material) of trimethyl-oxonium-(tetrafluoro-borate) salt and a "proton-sponge" together (SNAP reaction). This method is long and expensive, removal of the excess of the "proton-sponge" is difficult, multiple purification of the product is necessary in many cases. The epoxide formation on the double bond in position 5(10) resulted in—according to NMR spectroscopy—four types of epoxides, from which only 66% was the desired 5α,10α-epoxide. Despite the fact, that the crude product contained about 34% undesired product (β-epoxide) this was used in the Grignard reaction. The 4-bromo-dimethylaniline was used in five-fold excess in the Grignard reaction, which favored the formation of the monomethyl derivative and the dimerization of the reagent, therefore the work-up procedure and the isolation of the product were difficult, the isolated yield of the product was lower. From strategic point of view epoxidation—resulting a crude mixture—in the seventh step of the reaction sequence is not economical. Flash chromatography was used in 4 steps of the 11-step synthesis. During the isolation and purification of the intermediates ether was used in several cases, which is dangerous in case of industrial realization. The yield of the final product was diminished because of the purification steps, therefore the overall yield of the synthesis was only 3.22%.

Schemes 1 and 2 of the patent WO 01/47945 show further two the reaction sequences of the synthesis of compound CDB-4124.

The starting material of both synthesis was 3,3-[1,2-ethandiyl-bis(oxy)]-17α-hydroxy-oestr-5(10),9(11)-dien-17β-carbonitrile, which was silylated according to method described above, but the 21-halogen derivatives—chloro and bromo—were also synthesized in the same reaction mixture. The next steps, the replacement of the bromo atom for acetoxy group and the hydrolysis, were identical with the known methods. The further steps of synthesis shown on Scheme 1 are identical with the ones described in the previous patent.

According to Scheme 2 the 3-monoketal derivative of the 21-hydroxy derivative was synthesized, followed by the SNAP reaction for the introduction of 21-methoxy function and the keto group in position 20 (temporary protection) by reduction with lithium tetrahydrido aluminate. Epoxide formation was carried out at position 5(10) of the obtained 20-hydroxy derivative. Opening of the epoxide ring and removal of the ketal group was identical with the previously described methods. Iodo-oxy-benzoic acid was used for the re-oxidation of the hydroxyl group in position 20. The final step, the synthesis of the 17-acetoxy desired product, was carried out according to the method described in Scheme 1. This synthesis was accomplished in 12 steps, in 3.89% overall yield.

Although combination of the first two steps of the synthesis was a good solution, but for example the formation of the epoxide derivative—because of the purification step, which resulted in diminished yield—in a later phase of the reaction sequence was not up-to-date, expensive. Further disadvantageous solution was that flash chromatography was used for the purification of the intermediates and the final product. In several cases isolation of the products was carried out by treatment with ether, which can not be used in a large scale synthesis. Introduction of the methoxy group was carried out in several steps as described before. Removing of the "proton-sponge" used in the SNAP reaction could only be accomplished by repeated purification. Reduction with lithium tetrahydrido aluminate—which was used for the temporary protection of the oxo function in position 20—is especially dangerous in industrial scale. Further on regeneration of the oxo group in position 20 by oxidation with iodo-oxy-benzoic acid is expensive, therefore it is not suitable for industrial realization.

According to the above mentioned facts, there is no such known process, which is suitable for the realization of the synthesis of CDB-4124 on industrial scale using simple reaction conditions. Our aim was to elaborate a process, which is easy to scale-up, the industrial realization of which is safe, economical and the purity of the active ingredient fulfils the requirements of the pharmacopoeia.

Surprisingly it was found, that the following process fulfils the above mentioned requirements:

i) epoxide formation on the double bond in position 5(10) of 3,3-[1,2-ethandiyl-bis(oxy)]-oestr-5(10),9(11)-dien-17-one of formula (II)

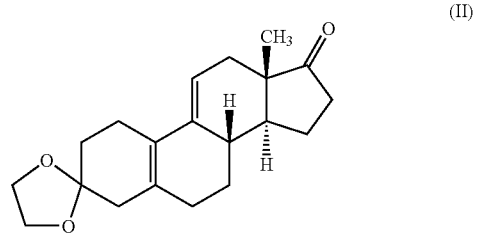

with hydrogen peroxide;

ii) addition of hydrogen cyanide formed in situ on position 17 of the obtained 5,10α-epoxy-3,3-[1,2-ethandiyl-bis(oxy)]-5α-oestr-9(11)-en-17-one of formula (III)

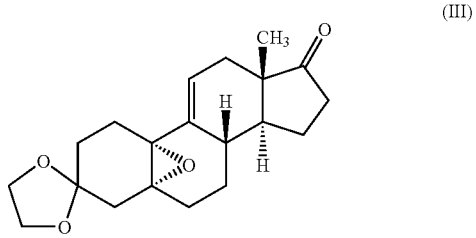

iii) silylation of the hydroxyl group in position 17 of the formed 5,10α-epoxy-3,3-[1,2-ethandiyl-bis(oxy)]-17α-hydroxy-5α-oestr-9(11)-en-17β-carbonitrile of formula (IV)

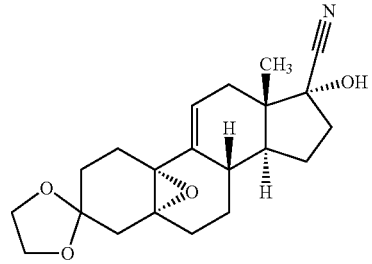

(IV)

with trimethyl chlorosilane;

iv) reacting the obtained 5,10α-epoxy-3,3-[1,2-ethandiyl-bis(oxy)]-17-[trimethyl-silyl-oxy]-5α-oestr-9(11)-en-17β-carbonitrile of formula (V)

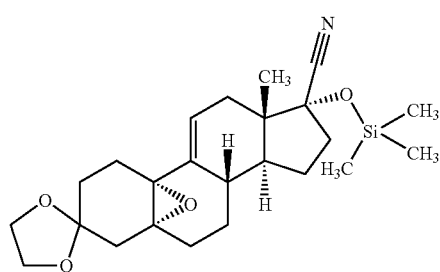

(V)

with 4-(dimethylamino)-phenyl magnesium bromide Grignard reagent in the presence of CuCl (Teutsch reaction);

v) silylation of the hydroxyl group in position 5 of the formed 11β-[4-(dimethyl-amino)-phenyl]-3,3-[1,2-ethandiyl-bis(oxy)]-5-hydroxy-17α-[trimethylsilyl-(oxy)]-5α-oestr-9-en-17β-carbonitrile of formula (VI)

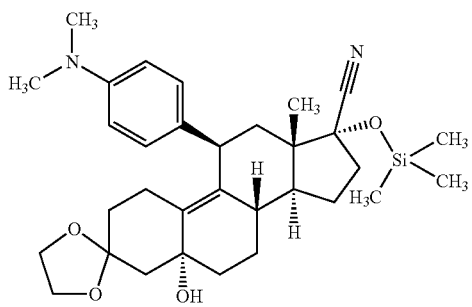

(VI)

with trimethyl chlorosilane;

vi) reacting the obtained 11β-[4-(dimethylamino)-phenyl]-3,3-[1,2-ethandiyl-bis(oxy)]-5,17α-bis-[trimethyl-silyl-(oxy)]-5α-oestr-9-en-17β-carbonitrile of formula (VII)

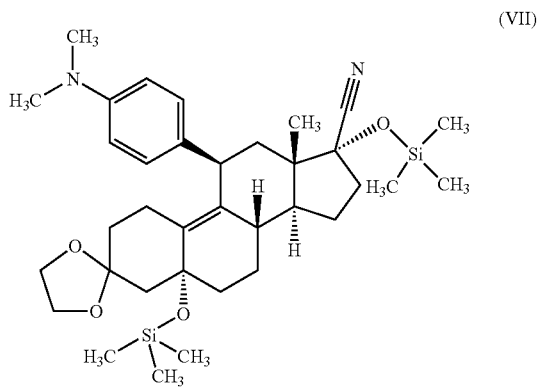

(VII)

with diisobutyl aluminum hydride and after addition of acid to the reaction mixture vii) methoxy-methylation of the obtained 11β-[4-(dimethylamino)-phenyl]-3,3-[1,2-ethandiyl-bis(oxy)]-5,17α-bis-[trimethyl-silyl-(oxy)]-5α-oestr-9-en-17β-carbaldehide of formula (VIII)

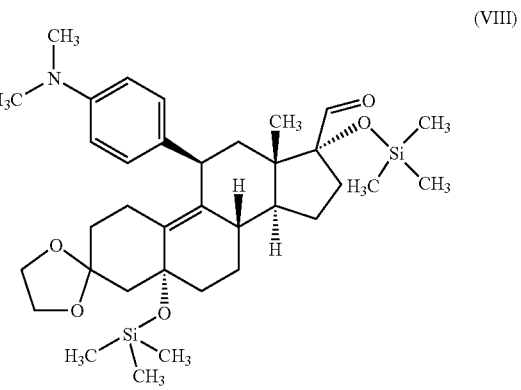

(VIII)

with methoxy-methyl Grignard reagent formed in situ, while hydrolyzing the trimethylsilyl protective groups;

viii) oxidation of the hydroxyl group in position 20 of the obtained 17,20ξ-dihydroxy-11β-[4-(dimethylamino)-phenyl]-21-methoxy-19-norpregna-4,9-dien-3-one of formula (IX)

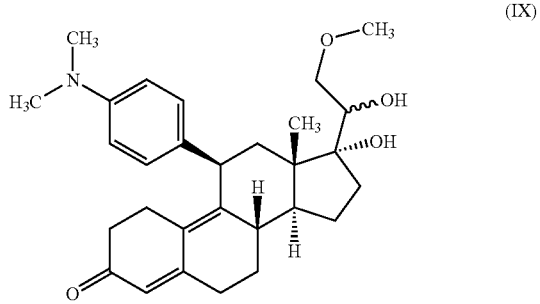

(IX)

with dicyclohexyl carbodiimide in the presence of dimethyl sulfoxide and a strong organic acid (Swern oxidation), and in given case after purification by chromatography ix) acetylation of the hydroxyl group in position 17 of the obtained 11β-[4-(dimethylamino)-phenyl]-17-hydroxy-21-methoxy-19-norpregna-4,9-dien-3,20-dione of formula (X)

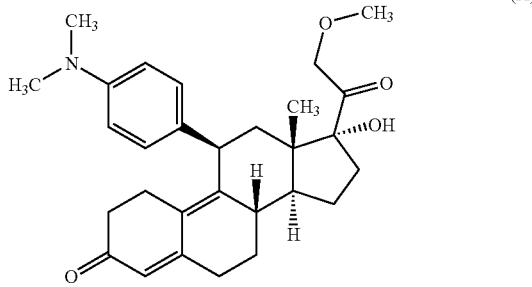

with acetic anhydride in the presence of perchloric acid, and in given case the obtained 7-acetoxy-11β-[4-(dimethylamino)-phenyl)]-21-methoxy-19-norpregna-4,9-dien-3,20-dione of formula (I) is purified by chromatography.

The keto-ketal of formula (II) is preferably reacted with 50% hydrogen peroxide solution in dry dichloromethane in the presence of pyridine and hexachloroacetone at 0-1° C. for 20-24 h. After completion of the reaction the mixture is diluted with dichloromethane, the excess of hydrogen peroxide is decomposed, the organic layer is separated, the aqueous phase is extracted twice with dichloromethane, the combined organic layers are washed with water, dried and concentrated. The oily residue is treated with a 1:3 mixture of ethyl acetate—diisopropyl ether.

The obtained keto-ketal-epoxide of formula (III)—the purity of which is 98.8% and contains 95.3% 5α,10α-epoxide according to HPLC—is used in step ii) without further purification.

Step ii) is preferably carried out by suspending the keto-ketal-epoxide of formula (III) in methanol, powdered potassium cyanide is added at 20-25° C., then after careful addition of acetic acid the reaction mixture is warmed to 50-55° C. The reaction mixture is cooled to 20-25° C. over a period of 1 h, then stirred at this temperature for 5 h. After completion of the reaction the mixture is diluted with water, stirred for 1 h and the precipitated crystalline epoxy-carbonitrile of formula (IV) is filtered off. The product can be used in step iii) without further purification.

In step iii) epoxy-carbonitrile of formula (IV) is preferably dissolved in dichloromethane with vigorous stirring, then after drying the water content is checked. Imidazole is added to the dry solution and trimethyl chlorosilane is added over a period of 1 h at 20-25° C. After completion of the reaction the solution is diluted with dichloromethane and the excess of trimethyl chlorosilane is decomposed by addition of water. The organic layer is separated, washed with water, dried and concentrated. The residue is crystallized from methanol, filtered and dried. The so obtained TMSO-carbonitrile of formula (V) (73.3%) can be used in the next step without further purification.

TMSO-carbonitrile of formula (V) formed in step iv) is preferably reacted the following way. First magnesium and 1,2-dibromo-ethane are added to dry tetrahydrofuran. The temperature of the reaction mixture starts to rise indicating the effectiveness of the activation. Then 4-bromo-dimethyl-aniline and a small amount of a solution of 1,2-dibromo-ethane in dry tetrahydrofuran and toluene are added to the stirred reaction mixture containing the magnesium (Grignard reagent). Reflux of the reaction mixture indicates the effectiveness of the activation. Then CuCl is added to the Grignard reagent solution and after 5 min stirring the mixture is cooled to 8-13° C. The solution of TMSO-carbonitrile in dichloromethane is added keeping the temperature between 10-15° C. After completion of the reaction the mixture is added to a stirred and cooled 10% solution of ammonium chloride containing alkali metal pyrosulfite. The warm solution is cooled to room temperature, diluted with dichloromethane, the organic layer is separated and the aqueous phase is extracted with dichloromethane. The combined organic layers are washed with water, treated with silicagel, dried over anhydrous sodium sulfate, filtered and concentrated in vacuum. The residue is crystallized from methanol. The crystalline product is isolated and dried. The obtained A-TMSO-carbonitrile of formula (VI) (80.79%) can be used in the next step without further purification.

Step v) is preferably carried out by dissolving the obtained A-TMSO-carbonitrile of formula (VI) in dichloromethane at 20-25° C., then after addition of imidazole the hydroxyl group in position 5 is silylated with trimethyl chlorosilane. The reaction time is about 2 h, then the mixture is diluted with dichloromethane and water, the organic layer is separated, washed with water, dried over anhydrous sodium sulfate, filtered and concentrated. The residue is treated with methanol, the obtained crystalline A-bis-TMSO-carbonitrile of formula (VII) (89.09%) is filtered off and dried. It can be used in the next step without further purification.

In step vi) the obtained A-bis-TMSO-carbonitrile of formula (VII) is dissolved in a mixture of methyl-tert-butyl ether and tetrahydrofuran, cooled to (−15)-(−20)° C. and 1 M DIBAL-H (diisobutyl aluminum hydride) solution in cyclohexane is added over a period of about 30 min while keeping the temperature, then the reaction mixture is stirred for further 1 h at this temperature. After completion of the reaction a 2:1 mixture of water and acetic acid is added at (−5)-(−10)° C., then the mixture is stirred for 20 min. The organic layer is separated, washed with water, 0.3 M sodium hydrogencarbonate solution and water. The organic layer is concentrated without drying at 40-45° C., the residue is dissolved in methanol and concentrated to given volume (see examples). The crystalline suspension is cooled to 5-10° C., filtered after 1 standing, washed with methanol of 0-(−5)° C. and dried. The obtained A-bis-TMSO-carbaldehyde of formula (VIII) (83.6%) can be used in the next step without further purification.

The obtained A-bis-TMSO-carbaldehyde of formula (VIII) in step vii) is transformed into 21-methoxy derivative with chain elongation. This is carried out by activating magnesium turnings as described above in dry tetrahydrofuran with 1,2-dibromo-ethane, then mercury(II) chloride is added to form amalgam. The mixture is diluted with toluene, then the activity of the amalgam is checked as described in Examples 7, 8 and 19. After checking the activity of the reactant a solution of methoxy-methyl chloride in toluene is added. Parallel to this the A-bis-TMSO-carbaldehyde is dissolved in toluene and the solution is added to the amalgam solution over a period of 30 min at 0-5° C. After completion of the reaction the mixture is added to a 1 M aqueous solution of potassium hydrogen sulfate keeping the temperature below 30° C. After stirring for 2 h, the layers are separated, the aqueous phase is added to a mixture of 1 M sodium hydrogencarbonate solution and dichloromethane and stirred for 10-15 min. The organic layer is separated, the aqueous phase is extracted with dichloromethane, the combined organic layers are dried, treated with charcoal, filtered and concentrated. The residue is the solid diol of formula (IX) (84.1%), which can be used in the next step without further purification.

The obtained diol of formula (IX) is further reacted according to step viii) of the invention. It is preferably dissolved in dry toluene and under nitrogen dimethyl sulfoxide, pyridine and trifluoroacetic acid are added at 20-25° C. Then a solution of dicyclohexyl carbodiimide in toluene is added to the mixture (Swern oxidation). The reaction mixture is stirred at 40° C. for 2 h, then cooled to 20-25° C. and 1 M aqueous solution of potassium hydrogen sulfate is added. After stirring for 30 min the precipitated crystalline compound is filtered off and washed with 1 M aqueous solution of potassium hydrogen sulfate. The two phases of the filtrate are separated, the aqueous phase is added to a 1 M solution of sodium hydroxide, the precipitated crude product is filtered off, washed water and dried. The obtained keton of formula (X) (79.5%) is used in next step after purification.

The synthesis of pure CDB-4124 of formula (I), which fulfils the purity requirements of the therapeutic application, contains two HPLC purification steps. The first one is the purification of the keton of formula (X). Acetylation of the purified keton of formula (X) leads to the crude CDB-4124, purification of the latter by HPLC yields the active ingredient of 99% purity.

Chromatography of keton of formula (X) and the crude CDB-4124 is preferably carried out using silicagel as bed and a 53:35:12 mixture of cyclohexane-methyl-tert-butyl ether-acetone as eluent both in the laboratory and the industrial process. n-Hexane and n-heptane can also be used instead of cyclohexane. The ratio of the solvent component in the eluent can vary within defined limits (cyclohexane, n-hexane, n-heptane:40-60%; methyl-tert-butyl ether: 25-45%; acetone: 10-20%).

In the end of step viii) keton of formula (X) is preferably purified the following way: silicagel adsorbent (ZEOPREP C-GEL C-490L, made by ZEOCHEM; 15-35 μm of particle size; bed length about 60 cm) is filled to an HPLC column with slurry packing method and the column is equilibrated with the eluent (a 53:35:12 mixture of cyclohexane—methyl-tert-butyl ether—acetone). The crude keton of formula (X) is dissolved in a mixture of acetone and methyl-tert-butyl ether and cyclohexane is added to the solution. The so obtained solution is filtered and injected on the column. UV detection is used. The first fraction is separated and the fractions containing the pure compound are collected and concentrated. According to an other method after concentration of the fractions dichloromethane is distilled off from the residue and the product is dissolved in dichloromethane. Content of impurities in both cases: less than 4%. This dichloromethane solution can be used in the next step.

CDB-4124 of formula (I) is synthesized from the purified keton of formula (X) according to step ix) of the present invention using acetic anhydride in the presence of perchloric acid: 70% perchloric acid is added to stirred and cooled ((−20)-(−25)° C.) acetic anhydride at such a rate to keep the temperature below (−15)° C. Then a solution of the purified 11β-[4-(dimethylamino)-phenyl)]-17-hydroxy-21-methoxy-19-norpregna-4,9-dien-3,20-dione of formula (X) in dichloromethane is added. After completion of the reaction the mixture is diluted with dichloromethane, cooled to (−10)° C. and water is added to decompose the acetic anhydride. The pH of the mixture is adjusted to 7-8 by addition of ammonium hydroxide solution. Then the aqueous phase is separated, extracted with dichloromethane, the combined organic layers are washed with water, dried and concentrated. The obtained crude final product, CDB-4124 of formula (I) is purified by HPLC according to the method described above.

The advantages of the process of the present invention compared to the known methods can be summarized in the followings:

a) The starting material of the synthesis [the keto-ketal of formula (II)] can easily be synthesized from oestr-4-en-3,17-dione by known methods.

b) According to our process epoxide formation on the double bond in position 5(10) is the first step of the synthesis. From the formed isomeric mixture of epoxides only the 5α,10α-epoxide leads to the desired compound, accordingly the other isomers are waste products.

According to our process this step resulting in high amount of loss of material is carried in the beginning of the reaction sequence, therefore the loss of material comes from the starting material and not from an intermediate of a later step, which is much more valuable. The process of our invention is more economical. Further disadvantage of the epoxidation step carried out in a later step of the reaction sequence of the known procedures is that the purification of the obtained compound is more difficult.

c) According to our process introduction of the strategically important 21-methoxy group is carried out in two steps via the new intermediates of formula (VII) and (VIII). Application of the new intermediate of formula (VII) made possible the formation of the aldehyde group in position 21 and the obtained new compound of formula (VIII) guaranteed the simple and industrially applicable introduction of the methoxy group in position 21. The silylated cyan-hydrine of formula (VII) is reacted with a solution of DIBAL-H in cyclohexane to furnish A-bis-TMSO-carbaldehyde of formula (VIII), which is reacted with methoxy-methyl chloride or bromide in a Grignard type reaction to yield the diol of formula (IX). Oxidation of the 20-hydroxy derivative formed in the Grignard reaction to the 20-keto derivative is carried out by Swern oxidation—instead of iodo-oxy-benzoic acid, which is used according to the literature—with dicyclohexyl carbodiimide in the presence of dimethyl sulfoxide and a strong organic acid. The advantage of the process our invention is that the applied reagent is stable and its use is economical.

d) The starting material of the procedures described in the literature is the silylated cyan-hydrine, from which the 21-methoxy derivative was synthesized in four steps consequently in a roundabout way. The cyan-hydrine was transformed into 21-chloro or 21-bromo derivative with lithium diisopropyl amide at −78° C., then the halogen substituents were exchanged for acetoxy group and the latter was hydrolyzed to yield the 21-hydroxy derivative, which was reacted with trimethyl-oxonium-tetrafluoroborate (using "proton-sponge") in SNAP reaction to furnish the 21-methoxy derivative.

e) There are no dangerous reactants such as lithium aluminum hydride and extremely flammable solvents such as ether in the process of our invention.

f) Further advantage of the process of our invention is that the formed intermediates in most cases are pure enough to use in the next steps without purification.

g) Although purification by chromatography is used only in the last two steps of the process of our invention the purity of the obtained active ingredient CDB-4124 is 99%, which fulfills the requirements of the therapeutic application.

h) Further advantage of the process of our invention is that the yields of the individual reaction steps are high (48.65%; 73.36%; 80.79%; 89.09%; 83.6%; 84.1%; 99.56%; 83.78%). The overall yield of the 11-step synthesis is 8.23%, contrarily to the overall yields of the known procedures (3.22% and 3.89%).

i) The reaction conditions used in some of the reaction steps of the process of our invention differ from the ones used in the known procedures, therefore the yields and the purity of the obtained products are higher. For example in the Grignard reaction—substitution of position 11—the ratio of the steroid starting material and 4-bromo-dimethyl-aniline is 1:1.25 contrarily to 1:5, which is used in the known procedures. This way realization of the reaction is less expensive and isolation of the product is easier, because less impurity is formed.

The process according to our invention is illustrated by the following not limiting examples.

EXAMPLE 1

5,10α-Epoxy-3,3-[1,2-ethandiyl-bis(oxy)]-5α-oestr-9(11)-en-17-one [compound of formula (III)]

Under nitrogen, 3,3-[1,2-ethandiyl-bis(oxy)]-o estr-5(10),9(11)-dien-17-one (46.7 g, 149 mmol) was dissolved with vigorous stirring in a mixture of pyridine (2.46 ml, 0.2 mol-equivalent) and dichloromethane (234 ml) and the solution was cooled to (−6)-(−8)° C. After addition of hexachloroacetone (5.46 ml, 35.95 mmol) 50% hydrogen peroxide of 0-(−2)° C. (60 ml, 1058 mmol) was added to the stirred solution at such a rate to keep the temperature below 0° C. The reaction mixture was stirred at 1-(−1)° C. for 20-24 h, then diluted with dichloromethane of 0-5° C. (390 ml), the excess of hydrogen peroxide was decomposed by addition of a solution of sodium thiosulfate pentahydrate (327 g, 1318 mmol, 8.87 mol-equivalent) in ice-cold water (1500 ml). The reaction mixture was stirred for 1.5 h, then the organic phase was separated. The aqueous phase was extracted with dichloromethane, the combined organic layers were washed with water, dried over anhydrous sodium sulfate, filtered and concentrated. The oily residue was crystallized from a 1:3 mixture of ethyl acetate—diisopropyl ether (435 ml), which contained 0.1% of pyridine. The so obtained product was dried to yield 23.87 g (48.66%) of the title compound. The purity of the title compound was 98.5-98.8% (determined by HPLC); which contained 95.3% of α-epoxide.

Melting point: 153-155° C.
$[\alpha]_D^{25}$=127.5° (c=1%, chloroform)
NMR: $^1$H NMR (500 MHz, CDCl$_3$ (TMS), δ (ppm)): 0.88 (3H, d, 18-CH$_3$); 1.91 (1H, dd, Hx-4); 2.17 (1H, d, Hy-4); 3.86-3.98 (4H, m, O—CH$_2$—CH$_2$-0); 6.05 (1H, m, H-11)
$^{13}$C NMR (125 MHz, CDCl$_3$ (TMS), δ (ppm)): 14.8 (C-18); 40.3 (C-4); 60.1 (C-10); 61.6 (C-5); 64.1 & 64.3 (O—CH$_2$—CH$_2$—O); 107.0 (C-3); 125.7 (C-11); 136.7 (C-9); 221.1 (C-17)

EXAMPLE 2

5,10α-Epoxy-3,3-[1,2-ethandiyl-bis(oxy)]-17α-hydroxy-5α-oestr-9(11)-en-17β-carbonitrile [compound of formula (IV)]

5,10α-Epoxy-3,3-[1,2-ethandiyl-bis(oxy)]-5α-oestr-9(11)-en-17-one (33 g, 0.1 mol) obtained in Example 1 was suspended in methanol (132 ml), then powdered potassium cyanide (19.5 g, 0.3 mol) was added at 20-25° C. After careful addition of acetic acid (11.5 ml, 0.2 mol) the heterogeneous reaction mixture was warmed to 55° C. over a period of 15 min, then cooled to 25° C. over a period of 1 h, and stirred at this temperature for further 5 h. After completion of the reaction water (132 ml) was added over a period of 30 min, the obtained crystalline product was filtered, washed with water and used in the next step without drying. The melting point of the dried sample: 143-144° C.
$[\alpha]_D^{25}$=+13.5° (c=1%, chloroform)
NMR: $^1$H NMR (500 MHz, CDCl$_3$ (TMS), δ (ppm)): 0.93 (3H, s, 18-CH$_3$); 3.09 (1H, s, OH); 3.86 & 3.98 (4H, m, O—CH$_2$—CH$_2$—O); 6.07 (1H, m, H-11)
$^{13}$C NMR (125 MHz, CDCl$_3$ (TMS), δ (ppm)): 16.8 (C-18); 60.2 (C-10); 61.9 (C-5); 64.0 & 64.2 (O—CH$_2$—CH$_2$—O); 77.3 (C-17); 106.9 (C-3); 120.7 (C-20); 125.9 (C-11); 135.7 (C-9)

EXAMPLE 3

5,10α-Epoxy-3,3-[1,2-ethandiyl-bis(oxy)]-17α-[(trimethyl-silyl)-oxy]-5α-oestr-9(11)-en-17β-carbonitrile [compound of formula (V)]

5,10α-Epoxy-3,3-[1,2-ethandiyl-bis(oxy)]-17α-hydroxy-5α-oestr-9(11)-en-17β-carbonitrile obtained in Example 2 was dissolved with vigorous stirring in dichloromethane (300 ml), the solution was dried over anhydrous sodium sulfate, then 200 ml of dichloromethane was distilled of from the solution. Imidazole (10.1 g, 0.148 mol) was added to the so obtained solution, then trimethyl chlorosilane (15.5 ml, 0-121 mol) was added dropwise at 20-25° C. over a period of 20 min. After stirring for 1 h, the solution was diluted with dichloromethane (66 ml) and water (66 ml). The organic layer was separated, washed with water, dried over anhydrous sodium sulfate, filtered and concentrated. The residue was treated with methanol (60 ml), cooled to 0° C., the precipitated crystalline product was filtered, washed with methanol of 0° C. and dried at 40° C. in vacuum to yield 31.5 g (73.36%) of the title compound. This product was used in the next reaction step.

Melting point: 167-170° C.
$[\alpha]_D^{25}$=+12.5° (c=1%, chloroform)
NMR: $^1$H NMR (300 MHz, CDCl$_3$ (TMS), δ (ppm)): 0.15 (9H, s, 17-O—Si(CH$_3$)$_3$); 0.83 (3H, d, 18-CH$_3$); 1.83 (1H, dd, H$_x$-4); 2.08 (1H, d, H$_y$-4); 3.76-3.94 (4H, m, O—CH$_2$—CH$_2$—O); 6.01 (1H, m, H-11)
$^{13}$C NMR (75 MHz, CDCl$_3$ (TMS), δ (ppm)): 0.9 (17-O—Si(CH$_3$)$_3$); 16.3 (C-18); 40.1 (C-4); 59.9 (C-10); 61.5 (C-5); 63.9 & 64.1 (O—CH$_2$—CH$_2$—O); 78.2 (C-17); 106.8 (C-3); 120.5 (C-20); 126.3 (C-11); 135.4 (C-9)

EXAMPLE 4

11β-[4-(Dimethylamino)-phenyl)]-3,3-[1,2-ethandiyl-bis(oxy)]-5-hydroxy-17α-[(trimethyl-silyl)-oxy]-5α-oestr-9-en-17β-carbonitrile [compound of formula (VI)]

Under nitrogen, magnesium turnings (3.3 g, 0.136 mol), dry tetrahydrofuran (24 ml) and 1,2-dibromo-ethan (0.12 ml, 0.00131 mol) were added to a flask equipped with stirrer, thermometer, dropping funnel, gas inlet and outlet at 20-25° C. After stirring for 5-10 min, the temperature started to rise indicating the effectiveness of the activation.

Parallel the following solution was made at 25° C. under nitrogen: dry tetrahydrofuran (15 ml), dry toluene (84 ml), 4-bromo-N,N-dimethyl-aniline (25 g, 0.125 mol) and 1,2-dibromo-ethane (0.16 ml, 0.00186 mol). 2 ml from this solution was added to the solution containing magnesium turnings, and the so obtained stirred reaction mixture was warmed to 60° C. If intensive reflux of the reaction mixture indicated the effectiveness of the activation, then the rest of the solution of 4-bromo-N,N-dimethyl-aniline was added dropwise after cooling, and the temperature was kept at 14-16° C. for further 2 h with cooling.

Copper(I) chloride (0.4 g, 4.04 mmol) was added to the obtained Grignard reagent solution, then the reaction mixture was stirred at 20-25° C. for 5 min. After cooling to 8-13° C. 5,10α-epoxy-3,3-[1,2-ethandiyl-bis(oxy)]-17α-[(trimethyl-silyl)-oxy]-5α-oestr-9(11)-en-17β-carbonitrile (42.96 g, 0.1 mol) in dichloromethane (180 ml) was added dropwise to the stirred and cooled solution at such a rate to keep the temperature at 10-15° C. Then cooling was stopped and the reaction mixture was stirred for further 4 h.

After completion of the reaction, the mixture was added to a vigorously stirred solution of ammonium chloride (100 ml, 10% aqueous solution), which contained sodium pyrosulfite (0.4 g, 2.1 mmol), diluted with dichloromethane (100 ml), stirred and settled. After separating the organic layer, the water phase was extracted with dichloromethane, the combined organic layers were washed with water, dried over anhydrous sodium sulfate, filtered and concentrated. The residue was recrystallized from methanol to yield 44.5 g (80.79%) of the title compound.

Melting point: 243-256° C.

$[\alpha]_D^{25}=-12.4°$ (c=1%, chloroform)

NMR: $^1$H NMR (300 MHz, CDCl$_3$ (TMS), δ (ppm)): 0.24 (9H, s, 17-O—Si(CH$_3$)$_3$); 0.55 (3H, s, 18-CH$_3$); 1.67 (1H, d, H$_x$-4); 2.02 (1H, dd, H$_y$-4); 2.91 (6H, s, N—CH$_3$); 3.87-4.07 (4H, m, O—CH$_2$—CH$_2$—O); 4.29 (1H, d, H-11); 4.42 (1H, d, OH); 6.64 (2H, m, H-3' & H-5'); 7.05 (2H, m, H-2' & H-6')

$^{13}$C NMR (75 MHz, CDCl$_3$ (TMS), δ (ppm)): 1.1 (17-O—Si(CH$_3$)$_3$); 16.9 (C-18); 38.8 (C-11); 40.7 (N—CH$_3$); 47.5 (C-4); 64.1 & 64.5 (O—CH$_2$—CH$_2$—O); 70.1 (C-5); 78.9 (C-17); 108.8 (C-3); 112.6 (C-3' & C-5'); 121.0 (C-20); 127.6 (C-2' & C-6'); 133.9, 134.0, 134.1 (C-9, C-10, C-1'); 148.4 (C-4')

The so obtained product was used the next step without further purification.

EXAMPLE 5

11β-[4-(Dimethylamino)-phenyl)]-3,3-[1,2-ethandiyl-bis(oxy)]-5,17α-bis-[(trimethyl-silyl)-oxy]-5α-oestr-9-en-17β-carbonitrile [compound of formula (VII)]

11β-[4-(Dimethylamino)-phenyl)]-3,3-[1,2-ethandiyl-bis(oxy)]-5-hydroxy-17α-[(trimethyl-silyl)-oxy]-5α-oestr-9-en-17β-carbonitrile (55 g, 0.1 mol) and imidazole (10.2 g, 0.15 mol) were dissolved with stirring in dichloromethane (225 ml) at 20-25° C. Trimethyl chlorosilane (15.75 ml, 0.123 mol) was added dropwise to the solution over a period of 20 min. During the addition of the reactant imidazole hydrochloride started to precipitate indicating the progress of the reaction. After stirring for 2 h the reaction mixture was diluted with dichloromethane (100 ml) and water (100 ml), stirred for a few minutes, settled, then the organic layer was separated, washed with water, dried over anhydrous sodium sulfate, filtered and concentrated. The residue was crystallized from methanol, the filtered product was dried in vacuum to yield 55.5 g (89.09%) of the title compound.

Melting point: 164-166° C.

$[\alpha]_D^{25}=+14.7°$ (c=1%, chloroform)

NMR: $^1$H NMR (300 MHz, DMSO-d$_6$ (TMS), δ (ppm)): 0.11 (9H, s, 17-O—Si(CH$_3$)$_3$); 0.22 (9H, s, 5-O—Si(CH$_3$)$_3$); 0.45 (3H, s, 18-CH$_3$); 1.63 (1H, d, H$_x$-4); 2.07 (1H, dd, Hy-4); 2.84 (6H, s, N—CH$_3$); 3.65-3.90 (4H, m, O—CH$_2$—CH$_2$—O); 4.21 (1H, d, H-11); 6.64 (2H, m, H-3' & H-5'); 7.03 (2H, m, H-2' & H-6')

$^{13}$C NMR (75 MHz, DMSO-d$_6$ (TMS), δ (ppm)): 0.9 (17-O—Si(CH$_3$)$_3$); 2.5 (5-O—Si(CH$_3$)$_3$); 16.7 (C-18); 37.8 (C-11); 40.1 (N—CH$_3$); 48.6 (C-4); 62.7 & 64.0 (O—CH$_2$—CH$_2$—O); 73.0 (C-5); 78.5 (C-17); 107.6 (C-3); 112.3 (C-3' & C-5'); 120.7 (C-20); 127.4 (C-2' & C-6'); 132.3, 133.2, 134.9 (C-9, C-10, C-1'); 148.1 (C-4')

EXAMPLE 6

11β-[4-(Dimethylamino)-phenyl)]-3,3-[1,2-ethandiyl-bis(oxy)]-5,17α-bis-[(trimethyl-silyl)-oxy]-5α-oestr-9-en-17β-carbaldehyde [compound of formula (VIII)]

Under nitrogen, 11β-[4-(dimethylamino)-phenyl)]-3,3-[1,2-ethandiyl-bis-(oxy)]-5,17α-bis-[(trimethyl-silyl)-oxy]-5α-oestr-9-en-17β-carbonitrile (40 g, 62.4 mmol) was dissolved in a mixture of methyl-tert-butyl ether (220 ml) and tetrahydrofuran (17 ml). The solution was cooled to (-15)-(-20)° C., then 1 M DIBAL-H (diisobutyl-aluminum hydride) solution in cyclohexane (160 ml) was added over a period of 30 min. at (-15)-(-20)° C. The reaction mixture was stirred for 1 h, then a mixture of water (160 ml) and acetic acid (80 ml) of (-5)-(-10)° C. was added with vigorous stirring under nitrogen over a period of 15-20 min. The so obtained reaction mixture was stirred at 20-25° C. for 30 min, then the organic layer was separated, washed with water (200 ml), 0.3 M sodium hydrogencarbonate solution (2×200 ml) and water (200 ml). The organic layer was concentrated without drying in vacuum at 40-45° C. The residue was dissolved in methanol (140 ml) and concentrated to a volume of 30 ml in vacuum. The obtained crystalline suspension was cooled to 5-10° C., filtered after 1 h standing, washed and dried below 60° C. in vacuum to yield 33.6 g (83.6%) of the title compound, which was used in the next step.

Melting point: 154-158° C.

$[\alpha]_D^{25}=+7.7°$ (c=1%, chloroform).

NMR: $^1$H NMR (500 MHz, CDCl$_3$ (TMS), δ (ppm)): 0.12 (9H, s, 17-O—Si(CH$_3$)$_3$); 0.19 (9H, s, 5-O—Si(CH$_3$)$_3$); 0.33 (3H, s, 18-CH$_3$); 2.88 (6H, s, N—CH$_3$); 3.86 & 3.98 (4H, m, O—CH$_2$—CH$_2$—O); 4.21 (1H, m, H-11); 6.61 (2H, m, H-3' & H-5'); 7.00 (2H, m, H-2' & H-6'); 9.56 (1H, s, H-20)

$^{13}$C NMR (125 MHz, CDCl$_3$ (TMS), δ (ppm)): 1.9 (17-O—Si(CH$_3$)$_3$); 2.6 (5-O—Si(CH$_3$)$_3$); 15.7 (C-18); 38.8 (C-111); 40.7 (N—CH$_3$); 63.4 & 64.4 (O—CH$_2$—CH$_2$—O); 73.7 (C-5); 91.1 (C-17); 108.5 (C-3); 112.8 (C-3' & C-5'); 127.6 (C-2' & C-6'); 133.6 (C-10); 134.3 (C-1'); 135.9 (C-9); 148.3 (C-4'); 203.3 (C-20)

EXAMPLE 7

11β-[4-Dimethylamino-phenyl)]-17,20ξ-dihydroxy-21-methoxy-19-norpregna-4,9-dien-3-one [compound of formula (IX)]

Under nitrogen, magnesium turnings (4.2 g, 173 mmol), dry tetrahydrofuran (60 ml) and 1,2-dibromo-ethan (2.4 ml, 28 mmol) were added to a 500 ml, 4-necked flask equipped with stirrer, thermometer, dropping funnel, reflux condenser, gas inlet and outlet at 20-25° C. After stirring for a few minutes the mixture reached the reflux temperature. Then the reaction mixture was cooled to 35-40° C. and mercury(II) chloride (0.23 g, 0.85 mmol) was added, after stirring for 15 min the mixture was cooled to 20-25° C. and dry toluene (20 ml) was added. Methoxymethyl chloride (12.8 ml, 168 mmol) was dissolved in dry toluene (50 ml) and 6 ml of the so obtained solution was added to the mixture of the 4-necked flask. After a few minutes the temperature of the reaction mixture rose to 35° C. The reaction mixture was cooled to 0-(−5)° C. and the rest of the solution of methoxymethyl chloride in toluene was added over a period of 2-2.5 h keeping the temperature at 0-(−5)° C. After finishing the addition a solution of 11β-[(4-dimethylamino)-phenyl]-3,3-[(1,2-ethandiyl)-bis(oxy)]-5,17α-bis-[(trimethyl-silyl-(oxy)]-5α-oestr-9-en-17β-carb aldehyde (20.0 g, 32 mmol) in dry toluene (80 ml) was added over a period of 1 h while keeping the temperature at 0-(−5)° C. After completion of the reaction the reaction mixture was added to a 1 M aqueous solution of potassium hydrogen sulfate (200 ml) at such rate to keep the temperature below 30° C. The mixture was stirred at 20-25° C. for 2 h, then the organic layer was separated and washed with 1 M potassium hydrogen sulfate (1×10 ml). The combined aqueous phases were added to a stirred mixture of 1 M sodium hydrogencarbonate solution (225 ml) and dichloromethane (75 ml). After stirring for 10-15 min the organic layer was separated. The aqueous phase was extracted with dichloromethane (5×50 ml), the combined organic layers were dried over anhydrous sodium sulfate (2 g), filtered, washed with dichloromethane (2×20 ml) and the filtrate was stirred with charcoal (2.5 g) for 10 min. The charcoal was filtered off, washed with dichloromethane (2×20 ml) and the filtrate was concentrated to yield 12.51 g (84.1%) of the title compound.

Melting point: 105° C. (soften).
$[\alpha]_D^{25}$=+157.7° (c=1%, dichloromethane)
NMR: $^1$H NMR ((major diastereomer), 500 MHz, CDCl$_3$ (TMS), δ (ppm)): 0.49 (3H, s, 18-CH$_3$); 2.91 (6H, s, N—CH$_3$); 3.37 (3H, s, O—CH$_3$); 3.49 (1H, m, H$_x$-21); 3.57 (1H, m, H$_y$-21); 3.81 (1H, m, H-20); 4.30 (1H, m, H-11); 5.73 (1H, s, H-4); 6.67 (2H, m, H-3' & H-5'); 7.04 (2H, m, H-2' & H-6')
$^{13}$C NMR ((major diastereomer), 125 MHz, CDCl$_3$ (TMS), δ (ppm)): 16.5 (C-18); 39.5 (C-11); 40.7 (N—CH$_3$); 59.2 (O—CH$_3$); 71.9 (C-20); 74.9 (C-21); 84.4 (C-17); 112.8 (C-3' & C-5'); 122.5 (C-4); 127.6 (C-2' & C-6'); 128.6 (C-10); 132.0 (C-1'); 147.2 (C-9); 148.5 (C-4'); 157.1 (C-5); 199.7 (C-3)

EXAMPLE 8

11β-[4-(Dimethylamino)-phenyl)]-17,20ξ-dihydroxy-21-methoxy-19-norpregna-4,9-dien-3-one [compound of formula (IX)]

Under nitrogen, magnesium turnings (4.2 g, 173 mmol), dry tetrahydrofuran (60 ml) and 1,2-dibromo-ethan (2.4 ml, 28 mmol) were added to a 500 ml, 4-necked flask equipped with stirrer, thermometer, dropping funnel, reflux condenser, gas inlet and outlet at 20-25° C. After stirring for a few minutes the mixture reached the reflux temperature. Then the reaction mixture was cooled to 35-40° C. and mercury(II) chloride (0.23 g, 0.85 mmol) was added, after stirring for 15 min the mixture was cooled to 20-25° C. and dry toluene (20 ml) was added. Methoxymethyl bromide (13.7 ml, 168 mmol) was dissolved in dry toluene (50 ml) and 6 ml of the so obtained solution was added to the mixture of the 4-necked flask. After a few minutes the temperature of the reaction mixture rose to 30-35° C. The reaction mixture was cooled to 10-15° C. and the rest of the solution of methoxymethyl bromide in toluene was added over a period of 2-2.5 h keeping the temperature at 10-15° C. After finishing the addition a solution of 11β-[(4-dimethylamino)-phenyl]-3,3-[(1,2-ethandiyl)-bis(oxy)]-5,17α-bis-[(trimethyl-silyl-(oxy)]-5α-oestr-9-en-17β-carbaldehyde (20.0 g, 32 mmol) in dry toluene (80 ml) was added over a period of 1 h while keeping the temperature at 10-15° C. After completion of the reaction the reaction mixture was added to a 1 M aqueous solution of potassium hydrogen sulfate (200 ml) at such rate to keep the temperature below 30° C. The mixture was stirred at 20-25° C. for 2 h, then the organic layer was separated and washed with 1 M potassium hydrogen sulfate (1×10 ml). The combined aqueous phases were added to a stirred mixture of 1 M sodium hydrogencarbonate solution (225 ml) and dichloromethane (75 ml). After stirring for 10-15 min the organic layer was separated. The aqueous phase was extracted with dichloromethane (5×50 ml), the combined organic layers were dried over anhydrous sodium sulfate (2 g), filtered, washed with dichloromethane (2×20 ml) and the filtrate was stirred with charcoal (2.5 g) for 10 min. The charcoal was filtered off, washed with dichloromethane (2×20 ml) and the filtrate was concentrated to yield 10.76 g (72.3%) of the title compound.

A small sample of the product was stirred with n-pentane, melting point: 105° C. (glassy structure, soften).
$[\alpha]_D^{25}$=+157.7°(c=1%, dichloromethane)

EXAMPLE 9

11β-[4-(Dimethylamino)-phenyl)]-17-hydroxy-21-methoxy-19-norpregna-4,9-dien-3,20-dione [compound of formula (X)]

Under nitrogen, 17,20ξ-dihydroxy-11β-[(4-dimethylamino)-phenyl]-21-methoxy-19-norpregna-4,9-dien-3-one (11.94 g, 25.7 mmol) and dry toluene (68 ml) were added to a 500 ml, 4-necked flask equipped with stirrer, thermometer, dropping funnel, reflux condenser, gas inlet and outlet. Dry dimethyl sulfoxide (9.9 ml, 139.5 mmol), pyridine (2.9 ml, 36.0 mmol) and trifluoroacetic acid (0.99 ml, 12.85 mmol) were added to the so obtained solution at 20-25° C. Then a solution of dicyclohexyl carbodiimide (10.6 g, 51.4 mmol) in toluene (54 ml) was added to the reaction mixture and the so obtained mixture was stirred at 40° C. The reaction time was 3 h. After completion of the reaction the reaction mixture was cooled to 20-25° C. and 1 M potassium hydrogen sulfate solution (78 ml) was added. After stirring for 30 min the precipitated crystals were filtered off and washed with 1 M potassium hydrogen sulfate solution (4×19 ml). The two phases of the filtrate were separated, the aqueous phase was added to a 1 M sodium hydroxide solution (254 ml) at 10-20° C. After stirring for 30 min the precipitated crude product was filtered off, washed with water and dried to yield 9.45 g (79.5%) of the title compound.

Melting point: 105-110° C.
The crude product was purified by HPLC according to method described in the next example.
NMR: $^1$H NMR (500 MHz, DMSO-d$_6$ (TMS), δ (ppm)): 0.20 (3H, s, 18-CH$_3$); 2.82 (6H, s, N—CH$_3$); 3.26 (3H, s, O—CH$_3$); 4.20 (1H, d, H$_x$-21); 4.35 (1H, m, H-11); 4.49 (1H, d, H$_y$-21); 5.37 (1H, s, OH); 5.67 (1H, s, H-4); 6.62 (2H, m, H-3' & H-5'); 7.00 (2H, m, H-2' & H-6')
$^{13}$C NMR (125 MHz, DMSO-d$_6$ (TMS), δ (ppm)): 15.8 (C-18); 38.7 (C-11); 40.1 (N—CH$_3$); 58.3 (O—CH$_3$); 75.4 (C-21); 88.6 (C-17); 112.5 (C-3' & C-5'); 122.0 (C-4); 127.2 (C-2' & C-6'); 128.1 (C-10); 132.0 (C-1'); 146.6 (C-9); 148.2 (C-4'); 156.5 (C-5); 197.9 (C-3); 208.9 (C-20)

EXAMPLE 10

Purification of the crude 11β-[4-(dimethylamino)-phenyl)]-17-hydroxy-21-methoxy-19-norpregna-4,9-dien-3,20-dione [compound of formula (X)] by HPLC (laboratory scale)

Silicagel (510 g, ZEOPREP C-GEL C-490L, 15-35 μm of particle size; bed length about 60 cm) was filled to an axial bed compression HPLC column of 5 cm of diameter with slurry packing method and the column was equilibrated with a 45:40:15 mixture of cyclohexane-methyl-tert-butyl ether-acetone eluent. 10.0 g of the crude title compound (content of active ingredient: 80%) was dissolved in a mixture of acetone (30 ml) and methyl-tert-butyl ether (80 ml) and cyclohexane (90 ml) was added to the stirred solution. The so obtained solution was filtered and injected on the column. The product was eluted with 85 ml/min flow rate and UV detection was used. The first fraction was about 50 ml, the main fraction containing the pure title compound was about 600 ml. The solid title compound was obtained by concentration of the eluted main fraction.

Yield: 7.4 g (74%) of the pure title compound. Content of impurities: less than 4%.

Melting point: 108-110° C.

$[\alpha]_D^{25}$=+199.2° (c=1%, chloroform)

NMR: $^1$H NMR (500 MHz, DMSO-$d_6$ (TMS), δ (ppm)): 0.20 (3H, s, 18-CH$_3$); 2.82 (6H, s, N—CH$_3$); 3.26 (3H, s, O—CH$_3$); 4.20 (1H, d, H$_x$-21); 4.35 (1H, m, H-11); 4.49 (1H, d, H$_y$-21); 5.37 (1H, s, OH); 5.67 (1H, s, H-4); 6.62 (2H, m, & H-5'); 7.00 (2H, m, 11-2' & H-6')

$^{13}$C NMR (125 MHz, DMSO-$d_6$ (TMS), δ (ppm)): 15.8 (C-18); 38.7 (C-11); 40.1 (N—CH$_3$); 58.3 (O—CH$_3$); 75.4 (C-21); 88.6 (C-17); 112.5 (C-3' & C-5'); 122.0 (C-4); 127.2 (C-2' & C-6'); 128.1 (C-10); 132.0 (C-1'); 146.6 (C-9); 148.2 (C-4'); 156.5 (C-5); 197.9 (C-3); 208.9 (C-20)

EXAMPLE 11

17-Acetoxy-11β-[4-(dimethylamino)-phenyl)]-21-methoxy-19-norpregna-4,9-dien-3,20-dione [compound of formula (I)]

70% Perchloric acid (6 ml) was added to stirred and cooled ((−20)-(−25)° C.) acetic anhydride (45 ml) at such a rate to keep the temperature below (−15)° C. Then a solution of 11β-[4-(dimethylamino)-phenyl)]-17-hydroxy-21-methoxy-19-norpregna-4,9-dien-3,20-dione (15.5 g) in dichloromethane (60 ml) was added at (−20)-(−25)° C. After completion of the reaction—followed by thin layer chromatography—the reaction mixture was diluted with dichloromethane (50 ml), cooled to (−10)° C. and ion exchanged water (52 ml) was added to decompose the acetic anhydride. After stirring for 10 min 25% ammonium hydroxide solution (77 ml) was added at such rate to keep the temperature below 25°C. (pH=7-8). Then the precipitated carbamide by-product was filtered off, the aqueous phase was separated, extracted with dichloromethane (2×30 ml) and the combined organic layers were concentrated to yield 16.2 g (95.8%) of the title compound, which was purified by HPLC according to method described in the next example.

NMR: $^1$H NMR (500 MHz, CDCl$_3$ (TMS), δ (ppm): 0.40 (3H, s, 18-CH$_3$); 2.10 (3H, s, O—CO—CH$_3$); 2.90 (6H, s, N—CH$_3$); 3.41 (3H, s, O—CH$_3$); 4.09 (1H, d, H$_x$-21); 4.38 (1H, m, H-11); 4.29 (1H, d, Hy-21); 5.77 (1H, br, H-4); 6.62 (2H, m, H-3' & H-5'); 6.96 (2H, m, H-2' & H-6')

$^{13}$C NMR (125 MHz, CDCl$_3$ (TMS), δ (ppm)): 15.6 (C-18); 21.1 (O—CO—CH$_3$); (39.3 (C-11); 40.6 (N—CH$_3$); 59.4 (O—CH$_3$); 76.0 (C-21); 93.9 (C-17); 112.8 (C-3' & C-5'); 123.0 (C-4); 127.3 (C-2' & C-6'); 129.4 (C-10); 131.3 (C-1'); 145.5 (C-9); 148.7 (C-4'); 156.4 (C-5); 170.7 (O—CO—CH$_3$); 199.4 (C-3); 202.7 (C-20)

EXAMPLE 12

Purification of crude CDB-4124 by HPLC (eluent: cyclohexane:methyl-tert-butyl-ether:acetone=60:30:10) (laboratory scale) [compound of formula (I)]

Silicagel (510 g, ZEOPREP C-GEL C-490L, 15-35 μm of particle size; bed length about 60 cm) was filled to an axial bed compression HPLC column of 5 cm of diameter with slurry packing method and the column was equilibrated with a 60:30:10 mixture of cyclohexane-methyl-tert-butyl ether-acetone eluent. 5.1 g of the crude compound of formula (I) (CDB-4124) obtained in the previous example (content of impurities: less than 4%) was dissolved in the eluent (100 ml), filtered and injected on the column. The product was eluted with 85 ml/min flow rate and LTV detection was used. The first fraction was about 40 ml, the main fraction containing the pure CDB-4124 was about 560 ml. The solid title compound was obtained by concentration of the eluted main fraction. Yield: 4.25 g (83.33%), content of impurities: less than 0.5%.

Melting point: 118° C.

$[\alpha]_D^{25}$=+127.2° (c=1%, chloroform)

NMR: $^1$H NMR (500 MHz, CDCl$_3$ (TMS), δ (ppm)): 0.40 (3H, s, 18-CH$_3$); 2.10 (3H, s, O—CO—CH$_3$); 2.90 (6H, s, N—CH$_3$); 3.41 (3H, s, O—CH$_3$); 4.09 (1H, d, H$_x$-21); 4.38 (1H, m, H-11); 4.29 (1H, d, H$_y$-21); 5.77 (1H, br, H-4); 6.62 (2H, m, H-3' & H-5'); 6.96 (2H, m, H-2' & H-6')

$^{13}$C NMR (125 MHz, CDCl$_3$ (TMS), δ (ppm)): 15.6 (C-18); 21.1 (O—CO—CH$_3$); (39.3 (C-11); 40.6 (N—CH$_3$); 59.4 (O—CH$_3$); 76.0 (C-21); 93.9 (C-17); 112.8 (C-3' & C-5'); 123.0 (C-4); 127.3 (C-2' & C-6'); 129.4 (C-10); 131.3 (C-1'); 145.5 (C-9); 148.7 (C-4'); 156.4 (C-5); 170.7 (O—CO—CH$_3$); 199.4 (C-3); 202.7 (C-20)

EXAMPLE 13

5,10α-Epoxy-3,3-[1,2-ethandiyl-bis(oxy)]-5α-oestr-9(11)-en-17-one [compound of formula (III)]

Equipment: acid resistant steel reactor of 500 liters equipped with propeller stirrer of variable revolution speed, reflux condenser and thermometer.

Under nitrogen, 3,3-[1,2-ethandiyl-bis(oxy)]-oestr-5(10),9(11)-dien-17-one (21.0 kg) was dissolved with vigorous stirring in a mixture of pyridine (1.106 l, 0.2 mol-equivalent) and dry dichloromethane (105.2 l) and the solution was cooled to (−6)-(−8)° C. After addition of hexachloroacetone (2.455 l) 50% hydrogen peroxide of 0-(−2)° C. (26.97 l) was added to the stirred solution at such a rate to keep the temperature below 0° C. The reaction mixture was stirred at 1-(−1)° C. for 20-24 h, then diluted with dichloromethane of 0-5° C. (175 l), the excess of hydrogen peroxide was decomposed by addition of a solution of sodium thiosulfate pentahydrate (8.87 mol-equivalent) in ice-cold water (150 l). The reaction mixture was stirred for 1.5 h, then the organic phase was separated. The aqueous phase was extracted with dichloromethane, the combined organic layers were washed with water, dried over anhydrous sodium sulfate, filtered and concentrated. The oily residue was crystallized from a 1:3 mixture of ethyl acetate—diisopropyl ether (195.6 l), which contained 0.1% of pyridine. The so obtained product was dried to yield 11.500 kg (52.13%) of the title compound. The purity of the title compound was 98.5-98.9% (determined by HPLC); which contained 96.2% of α-epoxide.

Melting point: 151-154° C.

$[\alpha]_D^{25}$=125.0° (c=1%, chloroform)

EXAMPLE 14

5,10α-Epoxy-3,3-[1,2-ethandiyl-bis(oxy)]-17α-hydroxy-5α-oestr-9(11)-en-17β-carbonitrile [compound of formula (IV)]

Equipment: enameled reactor of 250 liters equipped with propeller stirrer of variable revolution speed, reflux condenser and thermometer.

5,10α-Epoxy-3,3-[1,2-ethandiyl-bis(oxy)]-5α-oestr-9 (11)-en-17-one (9.9 kg) obtained in Example 13 was suspended in methanol (39.6 l), then powdered potassium cyanide (5.85 kg, 0.3 mol) was added at 20-25° C. After careful addition of acetic acid (3.48 l) the heterogeneous reaction mixture was warmed to 55° C. over a period of 15 min, then cooled to 25° C. over a period of 1 h, and stirred at this temperature for further 5 h. After completion of the reaction water (39.6 l) was added over a period of 30 min, the obtained crystalline product was filtered, washed with water and used in the next step without drying. The melting point of the dried sample: 140-143° C.

$[\alpha]_D^{25}$=+13.0° (c=1%, chloroform)

EXAMPLE 15

5,10α-Epoxy-3,3-[1,2-ethandiyl-bis(oxy)]-17α-[(trimethyl-silyl)-oxy]-5α-oestr-9(11)-en-17β-carbonitrile [compound of formula (V)]

Equipment: enameled reactor of 250 liters equipped with propeller stirrer of variable revolution speed, reflux condenser and thermometer.

5,10α-Epoxy-3,3-[1,2-ethandiyl-bis(oxy)]-17α-hydroxy-5α-oestr-9(11)-en-17β-carbonitrile obtained in Example 14 was dissolved with vigorous stirring in dichloromethane (90 l), the solution was dried over anhydrous sodium sulfate, then 60 l of dichloromethane was distilled of from the solution. Imidazole (0.303 kg) was added to the so obtained solution, then trimethyl chlorosilane (7.2 l) was added dropwise at 20-25° C. over a period of 20 min. After stirring for 1 h, the solution was diluted with dichloromethane (19.8 l) and water (19.8 l). The organic layer was separated, washed with water, dried over anhydrous sodium sulfate, filtered and concentrated. The residue was treated with methanol (18 l), cooled to 0° C., the precipitated crystalline product was filtered, washed with methanol of 0° C. and dried at 40° C. in vacuum to yield 10.1 kg (78.4%) of the title compound. This product was used in the next reaction step without further purification.

Melting point: 167-170° C.

$[\alpha]_D^{25}$=+12.5° (c=1%, chloroform)

EXAMPLE 16

11β-[4-(Dimethylamino)-phenyl)]-3,3-[1,2-ethandiyl-bis(oxy)]-5-hydroxy-17α-[(trimethyl-silyl)-oxy]-5α-oestr-9-en-17β-carbonitrile [compound of formula (VI)]

Equipment: enameled reactor of 250 liters equipped with propeller stirrer of variable revolution speed, reflux condenser and thermometer.

Under nitrogen, magnesium turnings (0.768 kg), dry tetrahydrofuran (5.59 l) and 1,2-dibromo-ethan (27.94 ml) were added to the equipment at 20-25° C. After stirring for 5-10 min, the temperature started to rise indicating the effectiveness of the activation.

Parallel the following solution was made at 25° C. under nitrogen: dry tetrahydrofuran (3.5 l), dry toluene (19.6 l), 4-bromo-N,N-dimethyl-aniline (5.8 kg) and 1,2-dibromo-ethane (34.25 ml). 400 ml from this solution was added to the solution containing magnesium turnings, and the so obtained stirred reaction mixture was warmed to 60° C. Intensive reflux of the reaction mixture indicated the effectiveness of the activation, so the rest of the solution of 4-bromo-N,N-dimethyl-aniline was added dropwise after cooling, and the temperature was kept at 14-16° C. for further 2 h with cooling.

Copper(I) chloride (93.11 g) was added to the obtained Grignard reagent solution, then the reaction mixture was stirred at 20-25° C. for 5 min. After cooling to 8-13° C. 5,10α-epoxy-3,3-[1,2-ethandiyl-bis(oxy)]-17α-[(trimethyl-silyl)-oxy]-5α-oestr-9(11)-en-17β-carbonitrile (10.0 kg) in dichloromethane (42 l) was added dropwise to the stirred and cooled solution at such a rate to keep the temperature at 10-15° C. Then cooling was stopped and the reaction mixture was stirred for further 4 h.

After completion of the reaction, the mixture was added to a vigorously stirred solution of ammonium chloride (23.3 l, 10% aqueous solution), which contained sodium pyrosulfite (93.1 g), diluted with dichloromethane (23.3 l), stirred and settled. After separating the organic layer, the water phase was extracted with dichloromethane, the combined organic layers were washed with water, dried over anhydrous sodium sulfate, filtered and concentrated. The residue was recrystallized from methanol to yield 10.5 kg (85.71%) of the title compound.

Melting point: 243-256° C.

$[\alpha]_D^{25}$=−12.4° (c=1%, chloroform)

The so obtained product was used in the next step without further purification.

EXAMPLE 17

11β-[4-(Dimethylamino)-phenyl)]-3,3-[1,2-ethandiyl-bis(oxy)]-5,17α-bis-[(trimethyl-silyl)-oxy]-5α-oestr-9-en-17β-carbonitrile [compound of formula (VII)]

Equipment: enameled reactor of 250 liters equipped with propeller stirrer of variable revolution speed, reflux condenser and thermometer.

11β-[4-(Dimethylamino)-phenyl)]-3,3-[1,2-ethandiyl-bis (oxy)]-5-hydroxy-17α-[(trimethyl-silyl)-oxy]-5α-oestr-9-en-17β-carbonitrile (10.45 kg) and imidazole (1.93 kg) were dissolved with stirring in dichloromethane (42.75 l) at 20-25° C. Trimethyl chlorosilane (3.0 l) was added dropwise to the solution over a period of 20 min. During the addition of the reactant imidazole hydrochloride started to precipitate indicating the progress of the reaction. After stirring for 2 h the reaction mixture was diluted with dichloromethane (19 l) and water (19 l), stirred for a few minutes, settled, then the organic layer was separated, washed with water, dried over anhydrous sodium sulfate, filtered and concentrated. The residue was crystallized from methanol, the filtered product was dried in vacuum to yield 10.25 kg (87.0%) of the title compound.

Melting point: 164-166° C.
$[\alpha]_D^{25}$=+14.7° (c=1%, chloroform)

EXAMPLE 18

11β-[4-(Dimethylamino)-phenyl)]-3,3-[1,2-ethandiyl-bis(oxy)]-5,17α-bis-[(trimethyl-silyl)-oxy]-5α-oestr-9-en-17β-carbaldehyde [compound of formula (VIII)]

Equipment: enameled reactor of 250 liters equipped with propeller stirrer of variable revolution speed, reflux condenser and thermometer.

Under nitrogen, 11β-[4-(dimethylamino)-phenyl)]-3,3-[1,2-ethandiyl-bis-(oxy)]-5,17α-bis-[(trimethyl-silyl)-oxy]-5α-oestr-9-en-17β-carbonitrile (8 kg) was dissolved in a mixture of methyl-tert-butyl ether (44 l) and tetrahydrofuran (3.4 l). The solution was cooled to (−15)-(−20)° C., then 1 M DIBAL-H solution in cyclohexane (32 l) was added over a period of 30 min. at (−15)-(−20)° C. The reaction mixture was stirred for 1 h, then a mixture of water (32 l) and acetic acid (16 l) of (−5)-(−10)° C. was added with vigorous stirring under nitrogen over a period of 15-20 min. The so obtained reaction mixture was stirred at 20-25° C. for 30 min, then the organic layer was separated, washed with water (40 l), 0.3 M sodium hydrogencarbonate solution (2×40 l) and water (40 l). The organic layer was concentrated without drying in vacuum at 40-45° C. The residue was dissolved in methanol (28 l) and concentrated to a volume of 6 l in vacuum. The obtained crystalline suspension was cooled to 5-10° C., filtered after 1 h standing, washed and dried below 60° C. in vacuum to yield 6.95 kg (86.46%) of the title compound, which was used in the next step without further purification.

Melting point: 154-158° C.
$[\alpha]_D^{25}$=+7.7° (c=1%, chloroform)

EXAMPLE 19

11β-[4-(Dimethylamino)-phenyl)]-17,20ξ-dihydroxy-21-methoxy-19-norpregna-4,9-dien-3-one [compound of formula (IX)]

Equipment: enameled reactor of 250 liters equipped with propeller stirrer of variable revolution speed, reflux condenser and thermometer.

Under nitrogen, magnesium turnings (1.05 kg), dry tetrahydrofuran (15 l) and 1,2-dibromo-ethan (600 ml) were added to the reactor at 20-25° C. After stirring for a few minutes the mixture reached the reflux temperature. Then the reaction mixture was cooled to 35-40° C. and mercury(II) chloride (57.5 g) was added, after stirring for 15 min the mixture was cooled to 20-25° C. and dry toluene (5 l) was added. Methoxymethyl chloride (3.2 l) was dissolved in dry toluene (12.5 l) and 1.5 l of the so obtained solution was added to the reaction mixture. After a few minutes the temperature of the reaction mixture rose to 35° C. The reaction mixture was cooled to 0-(−5)° C. and the rest of the solution of methoxymethyl chloride in toluene was added over a period of 2-2.5 h keeping the temperature at 0-(−5)° C. After finishing the addition a solution of 11β-[(4-dimethylamino)-phenyl]-3,3-[(1,2-ethandiyl)-bis(oxy)]-5,17α-bis-[(trimethyl-silyl-(oxy)]-5α-oestr-9-en-17β-carbaldehyde (5.0 kg) in dry toluene (20 l) was added over a period of 1 h while keeping the temperature at 0-(−5)° C. After completion of the reaction the reaction mixture was added to a 1 M aqueous solution of potassium hydrogen sulfate (50 l) at such rate to keep the temperature below 30° C. The mixture was stirred at 20-25° C. for 2 h, then the organic layer was separated and washed with 1 M potassium hydrogen sulfate (1×2.5 l). The combined aqueous phases were added to a stirred mixture of 1 M sodium hydrogencarbonate solution (56 l) and dichloromethane (19 l). After stirring for 10-15 min the organic layer was separated. The aqueous phase was extracted with dichloromethane (5×12.5 l), the combined organic layers were dried over anhydrous sodium sulfate (500 g), filtered, washed with dichloromethane (2×2 l) and the filtrate was stirred with charcoal (625 g) for 10 min. The charcoal was filtered off, washed with dichloromethane (2×5 l) and the filtrate was concentrated to yield 3.3 kg (88.73%) of the title compound.

Melting point: 105° C. (soften).
$[\alpha]_D^{25}$=+156.2° (c=1%, dichloromethane).

EXAMPLE 20

11β-[4-(Dimethylamino)-phenyl)]-17-hydroxy-21-methoxy-19-norpregna-4,9-dien-3,20-dione [compound of formula (X)]

Equipment: enameled reactor of 250 liters equipped with propeller stirrer of variable revolution speed, reflux condenser and thermometer.

Under nitrogen, 17,20ξ-dihydroxy-11β-[(4-dimethylamino)-phenyl]-21-methoxy-19-norpregna-4,9-dien-3-one (3.2 kg) and dry toluene (18 l) were added to the reactor. Dry dimethyl sulfoxide (2.7 l), pyridine (0.78 l) and trifluoroacetic acid (0.265 l) were added to the so obtained solution at 20-25° C. Then a solution of dicyclohexyl carbodiimide (2.84 kg) in toluene (14.5 l) was added to the reaction mixture and the so obtained mixture was stirred at 40° C. The reaction time was 3 h. After completion of the reaction the reaction mixture was cooled to 20-25° C. and 1 M potassium hydrogen sulfate solution (21 l) was added. After stirring for 30 min the precipitated crystals were filtered off and washed with 1 M potassium hydrogen sulfate solution (4×5 l). The two phases of the filtrate were separated, the aqueous phase was added to a 1 M sodium hydroxide solution (68 l) at 10-20° C. After stirring for 30 min the precipitated crude product was filtered off; washed with water and dried to yield 2.556 kg (80.0%) of the title compound.

The crude product was purified by HPLC according to method described in the next example.

EXAMPLE 21

Purification of the crude 11β-[4-(dimethylamino)-phenyl)]-17-hydroxy-21-methoxy-19-norpregna-4,9-dien-3,20-dione [compound of formula (X)] by HPLC (industrial scale)

Silica gel (8 kg, ZEOPREP C-GEL C-490L, 15-35 μm of particle size; bed length about 60 cm) was filled to an axial bed compression HPLC column of 20 cm of diameter with slurry packing method and the column was equilibrated with a 53:34:12 mixture of cyclohexane-methyl-tert-butyl ether-acetone eluent. 160 g of the crude title compound (content of active ingredient: 80%) was dissolved in a mixture of acetone (0.48 l) and methyl-tert-butyl ether (1.28 l) and cyclohexane (1.44 l) was added to the stirred solution. The so obtained solution was filtered and injected on the column. The product was eluted with 80 l/h flow rate and UV detection was used. The first fraction was about 1 l, the main fraction containing the pure title compound was about 14 l. The solid title compound can be obtained by concentration of the eluted main fraction, but preferably after concentration of the main fraction dichloromethane was distilled off from the residue and the product was dissolved in dichloromethane. This dichloromethane solution was used in the next step.

Yield: 120 g (75%) of the pure, solid title compound or content of active ingredient of the dichloromethane solution. Content of impurities: less than 4%.

Melting point: 105-110° C.
$[\alpha]_D^{25} = +199.2°$ (c=1%, chloroform)

EXAMPLE 22

Crude 17-acetoxy-11β-[4-(dimethylamino)-phenyl)]-21-methoxy-19-norpregna-4,9-dien-3,20-dione [compound of formula (I)]

Equipment: enameled reactor of 250 liters equipped with propeller stirrer of variable revolution speed, reflux condenser and thermometer.

70% Perchloric acid (1.8 l) was added to stirred and cooled ((−20)-(−25)° C.) acetic anhydride (13.5 l) at such a rate to keep the temperature below (−15)° C. Then a solution of 11β-[4-(dimethylamino)-phenyl)]-17-hydroxy-21-methoxy-19-norpregna-4,9-dien-3,20-dione (4.65 kg) in dichloromethane (18 l) was added at (−20)-(−25)° C. After completion of the reaction—followed by thin layer chromatography—the reaction mixture was diluted with dichloromethane (15 l), cooled to (−10)° C. and ion exchanged water (15.5 l) was added to decompose the acetic anhydride. After stirring for 10 min 25% ammonium hydroxide solution (23 l) was added at such rate to keep the temperature below 25° C. (pH=7-8). Then the precipitated carbamide by-product was filtered off, the aqueous phase was separated, extracted with dichloromethane (2×9 l) and the combined organic layers were concentrated to yield 4.73 kg (93.79%) of the title compound (CDB-4124), which was purified by HPLC according to method described in the next example.

EXAMPLE 23

Purification of Crude CDB-4124 by HPLC (Industrial Scale) [Compound of Formula (I)]

Silicagel (8 kg, ZEOPREP C-GEL C-490L, 15-35 μm of particle size; bed length about 60 cm) was filled to an axial bed compression HPLC column of 20 cm of diameter with slurry packing method and the column was equilibrated with a 53:35:12 mixture of cyclohexane-methyl-tert-butyl ether-acetone eluent. 80 g of the crude compound of formula (I) (CDB-4124) obtained in the previous example (content of impurities: less than 4%) was dissolved in the eluent (1.6 l), filtered and injected on the column. The product was eluted with 80 l/h flow rate and UV detection was used. The first fraction was about 0.7 l, the main fraction containing the pure CDB-4124 was about 10 l. The solid title compound was obtained by concentration of the eluted main fraction or it can be obtained as methanol solution after concentration of the main fraction and dissolving the product in methanol. Yield: 70 g of the solid title compound or content of active ingredient of the methanol solution. Content of impurities: less than 0.5%.

Melting point: 118° C.
$[\alpha]_D^{25} = +127.2°$ (c=1%, chloroform)

What we claim is:
1. An industrial process for the synthesis of 17-acetoxy-11β-[4-(dimethylamino)-phenyl]-21-methoxy-19-norpregna-4,9-dien-3,20-dione of formula (I)

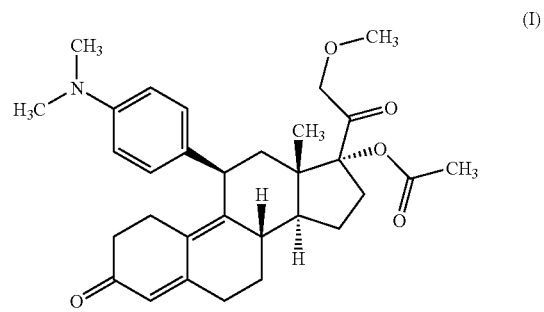

from 3,3-[1,2-ethandiyl-bis(oxy)]-oestr-5(10),9(11)-dien-17-one of formula (II),

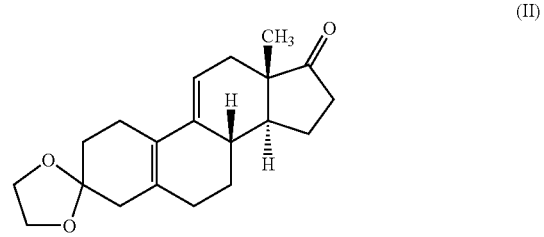

characterized by
 i) formation of an epoxide on the double bond in position 5(10) of 3,3-[1,2-ethandiyl-bis(oxy)]-oestr-5(10),9(11)-dien-17-one of formula (II)

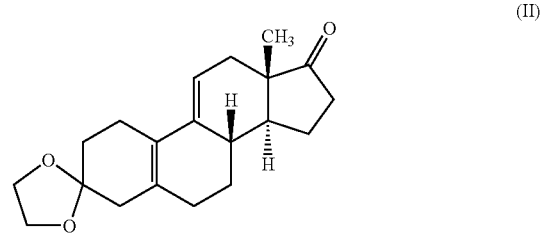

with hydrogen peroxide;
 ii) addition of hydrogen cyanide formed in situ on position 17 of the obtained 5,10α-epoxy-3,3-[1,2-ethandiyl-bis(oxy)]-5α-oestr-9(11)-en-17-one of formula (III)

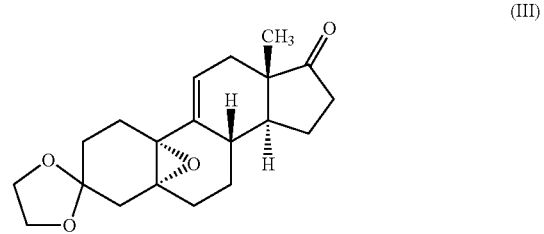

iii) silylation of the hydroxyl group in position 17 of the formed 5,10α-epoxy-3,3-[1,2-ethandiyl-bis(oxy)]-17α-hydroxy-5α-oestr-9(11)-en-17β-carbonitrile of formula (IV)

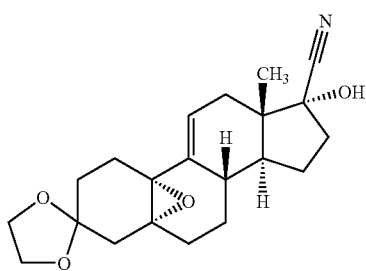
(IV)

with trimethyl chlorosilane;

iv) reacting the obtained 5,10α-epoxy-3,3-[1,2-ethandiyl-bis(oxy)]-17-[trimethyl-silyl-oxy]-5α-oestr-9(11)-en-17β-carbonitrile of formula (V)

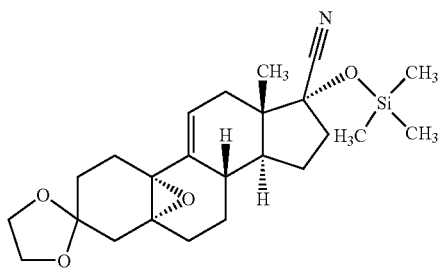
(V)

with 4-(dimethylamino)-phenyl magnesium bromide Grignard reagent in the presence of CuCl (Teutsch reaction);

v) silylation of the hydroxyl group in position 5 of the formed 11β-[4-(dimethyl-amino)-phenyl]-3,3-[1,2-ethandiyl-bis(oxy)]-5-hydroxy-17α-[trimethylsilyl-(oxy)]-5α-oestr-9-en-17β-carbonitrile of formula (VI)

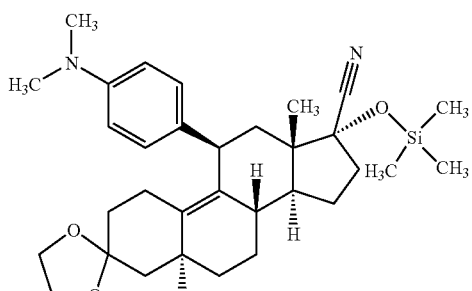
(VI)

with trimethyl chlorosilane;

vi) reacting the obtained 11β-[4-(dimethylamino)-phenyl]-3,3-[1,2-ethandiyl-bis(oxy)]-5,17α-bis-[trimethyl-silyl-(oxy)]-5α-oestr-9-en-17β-carbonitrile of formula (VII)

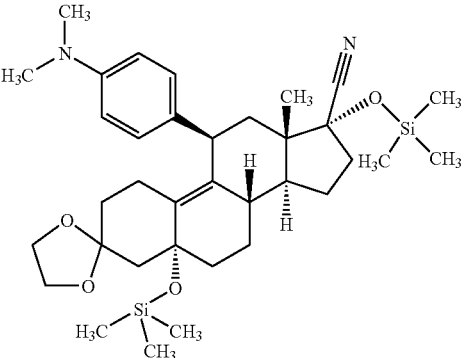
(VII)

with diisobutyl aluminum hydride and after addition of acid to the reaction mixture vii) methoxy-methylation of the obtained 11β-[4-(dimethylamino)-phenyl]-3,3-[1,2-ethandiyl-bis(oxy)]-5,17α-bis-[trimethyl-silyl-(oxy)]-5α-oestr-9-en-17β-carbaldehide of formula (VIII)

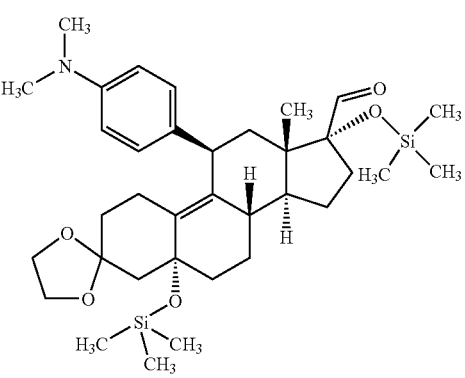
(VIII)

with methoxy-methyl Grignard reagent formed in situ, while hydrolyzing the trimethylsilyl protective groups;

viii) oxidation of the hydroxyl group in position 20 of the obtained 17,20ξ-dihydroxy-11β-[4-(dimethylamino)-phenyl]-21-methoxy-19-norpregna-4,9-dien-3-one of formula (IX)

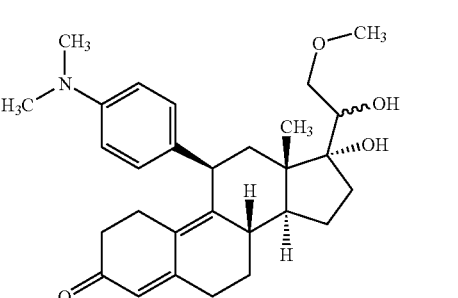
(IX)

with dicyclohexyl carbodiimide in the presence of dimethyl sulfoxide and a strong organic acid (Swern oxidation), and optionally purification by chromatography ix) acetylation of the hydroxyl group in position 17 of the obtained 11β-[4-(dimethylamino)-phenyl]-17-hydroxy-21-methoxy-19-norpregna-4,9-dien-3,20-dione of formula (X)

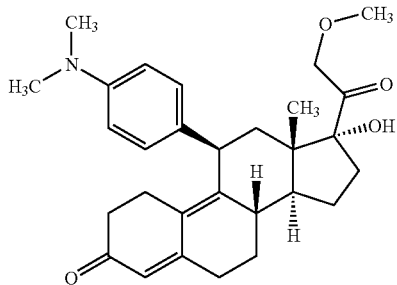

(X)

with acetic anhydride in the presence of perchloric acid, and optionally the obtained 7-acetoxy-11β-[4-(dimethylamino)-phenyl)]-21-methoxy-19-norpregna-4,9-dien-3,20-dione of formula (I) is purified by chromatography.

2. The process according to claim 1, characterized by using 0.25±0.025 equivalent excess of 4-(dimethylamino)-phenyl magnesium bromide Grignard reagent in step iv) as compared to 5,10α-epoxy-3,3-[1,2-ethandiyl-bis(oxy)]-17-[trimethyl-silyl-oxy]-5α-oestr-9(11)-en-17β-carbonitrile of formula (V).

3. The process according to claim 1, characterized by using trifluoroacetic acid as strong organic acid in step viii).

4. 11β-[4-(dimethylamino)-phenyl]-3,3-[1,2-ethandiyl-bis(oxy)]-5,17α-bis-[trimethyl-silyl-(oxy)]-5α-oestr-9-en-17β-carbaldehide.

5. 11β-[4-(dimethylamino)-phenyl]-3,3-[1,2-ehtndiyl-bis(oxy)]-5,17α-bis-[trimethyl-silyl-(oxy)]-5α-oestr-9-en-17β-carbaldehide.

* * * * *

UNITED STATES PATENT AND TRADEMARK OFFICE
CERTIFICATE OF CORRECTION

| | | |
|---|---|---|
| PATENT NO. | : 8,183,402 B2 | Page 1 of 1 |
| APPLICATION NO. | : 12/598163 | |
| DATED | : May 22, 2012 | |
| INVENTOR(S) | : Bódi et al. | |

It is certified that error appears in the above-identified patent and that said Letters Patent is hereby corrected as shown below:

Column 28, lines 14-16, Claim 4 should read
-- 4. 11β-[4-(dimethylamino)-phenyl]-3,3-[1,2-ethandiyl-bis(oxy)]-5,17α-bis-[trimethyl-silyl-(oxy)]-5α-oestr-9-en-17β-carbonitrile. --.

Column 28, lines 17-20, Claim 5 should read
-- 5. 11β-[4-(dimethylamino)-phenyl]-3,3-[1,2-ethandiyl-bis(oxy)]-5,17α-bis-[trimethylsilyl-(oxy)]-5α-oestr-9-en-17β-carbaldehide. --.

Signed and Sealed this
Thirty-first Day of July, 2012

David J. Kappos
*Director of the United States Patent and Trademark Office*